United States Patent
Laufer et al.

(10) Patent No.: US 8,034,062 B2
(45) Date of Patent: Oct. 11, 2011

(54) METHODS AND DEVICES FOR PLACEMENT OF AN INTRA-ABDOMINAL OR INTRA-THORACIC APPLIANCE THROUGH A NATURAL BODY ORIFICE

(75) Inventors: Michael D. Laufer, Menlo Park, CA (US); Amos G. Cruz, Franklin, MA (US); Thomas R. Cygan, Marlborough, MA (US); Jennifer Almy, Auburndale, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 581 days.

(21) Appl. No.: 12/107,746

(22) Filed: Apr. 22, 2008

(65) Prior Publication Data

US 2009/0018391 A1    Jan. 15, 2009

Related U.S. Application Data

(60) Provisional application No. 60/931,243, filed on May 21, 2007.

(51) Int. Cl.
*A61B 17/08* (2006.01)
*A61F 2/00* (2006.01)
*A61F 13/00* (2006.01)

(52) U.S. Cl. ............... 606/151; 606/157; 600/37

(58) Field of Classification Search ........ 600/37; 606/151, 157
See application file for complete search history.

(56) References Cited

U.S. PATENT DOCUMENTS

| | | |
|---|---|---|
| 5,074,868 A | 12/1991 | Kuzmak |
| 5,159,446 A | 10/1992 | Hibino et al. |
| 5,449,368 A | 9/1995 | Kuzmak |
| 6,494,888 B1 | 12/2002 | Laufer et al. |
| 6,572,629 B2 | 6/2003 | Kalloo et al. |
| 6,663,639 B1 | 12/2003 | Laufer et al. |
| 6,676,674 B1 | 1/2004 | Dudai |
| 6,966,875 B1 | 11/2005 | Longobardi |
| 7,841,347 B2 * | 11/2010 | Sonnenschein et al. ...... 128/898 |
| 2001/0049497 A1 * | 12/2001 | Kalloo et al. ............ 604/164.01 |
| 2002/0022851 A1 * | 2/2002 | Kalloo et al. ................. 606/151 |
| 2002/0169464 A1 * | 11/2002 | Latour ........................... 606/151 |
| 2003/0208212 A1 | 11/2003 | Cigaina |
| 2004/0102804 A1 | 5/2004 | Chin |
| 2005/0075652 A1 | 4/2005 | Byrum et al. |
| 2005/0261712 A1 | 11/2005 | Balbierz et al. |
| 2005/0277963 A1 | 12/2005 | Fields |
| 2005/0283235 A1 * | 12/2005 | Kugler et al. .............. 623/14.13 |
| 2006/0178564 A1 | 8/2006 | Jones et al. |
| 2006/0241653 A1 | 10/2006 | Jones et al. |
| 2006/0252983 A1 * | 11/2006 | Lembo et al. ................... 600/37 |
| 2007/0015956 A1 * | 1/2007 | Crawford et al. ............... 600/37 |
| 2007/0038239 A1 | 2/2007 | Ritchie |
| 2007/0218083 A1 * | 9/2007 | Brooks ...................... 424/239.1 |
| 2008/0208216 A1 | 8/2008 | Cerier |
| 2008/0319435 A1 | 12/2008 | Rioux et al. |
| 2009/0005797 A1 | 1/2009 | Laufer et al. |

FOREIGN PATENT DOCUMENTS

WO   WO-2007064906 A2   6/2007

* cited by examiner

*Primary Examiner* — Darwin Erezo
*Assistant Examiner* — Dianne Dornbusch
(74) *Attorney, Agent, or Firm* — Nutter McClennen & Fish LLP

(57) ABSTRACT

Natural orifice transenteric surgical methods and devices for placing a semi-circumferential appliance around a hollow bodily organ such as the stomach. In one alternative embodiment, such an appliance is placed in order to reduce the inner volume of the stomach.

7 Claims, 9 Drawing Sheets

METHODS AND DEVICES FOR PLACEMENT OF AN INTRA-ABDOMINAL OR INTRA-THORACIC APPLIANCE THROUGH A NATURAL BODY ORIFICE

CROSS-REFERENCE TO RELATED APPLICATION

This application claims the benefit of Provisional Patent Application No. 60/931,243, filed May 21, 2007, which is incorporated by reference herein in its entirety.

TECHNICAL FIELD OF THE INVENTION

Generally, the present invention is related to trans-luminal surgical devices and methods. More particularly, the devices and methods herein described provide for gastric restriction and volume reduction by the placement of an appliance on the outer surface of the stomach from access obtained via the inside of the stomach. These devices may also be used to place an appliance on other hollow bodily conduits or organs.

BACKGROUND OF THE FIELD OF THE INVENTION

Laparoscopic surgery has greatly reduced the size and scope of incisions made in a patient and resulted in reduced morbidity and mortality rates. However, even with the reductions in the size and extent of incisions as a result of laparoscopic surgery, complications in and during surgical procedures remain. A technique that is developing to further reduce surgical complications is to work through a natural orifice such as the mouth, to access the stomach, where a hole is made through the stomach wall, to gain access to the inside of the abdominal space outside of the stomach. This NOTES approach, or natural orifice transenteric surgery, allows scarless surgical procedures with faster recovery, fewer complications, and less pain.

Stomach tissue often needs surgical treatment to treat fistulas and to close trans-gastric incisions to stop stomach fluids from leaking from the stomach to surrounding tissue and to stop infectious matter from spreading from or to the stomach tissue. Other stomach treatments include stomach reduction procedures for obese patients. Traditionally, physicians have placed devices laparoscopically on the external surface of the gastric wall to create a restricted stomach capacity. Another traditional procedure for stomach reduction includes a laparoscopic procedure in which surgeons protrude into the abdomen from the exterior of the patient and staple the stomach into a smaller volume. This restriction creates a pouch inside the stomach which fills quickly when food is ingested and assists in generating a sensation of being full. However, these procedures have drawbacks such as complications from port punctures of the stomach, large incisions, substantial recovery time, expense, lost productive work time, infection, and the like.

However, the incision required by the current surgical procedures including laparoscopy, include a morbidity and mortality rate that can be reduced by reducing or eliminating the need for an incision by approaching the surgical site through endoluminal procedures.

In addition, dissecting through the posterior aspect of the abdomen can be treacherous because of nearby vascular structure and nerves that can be inadvertently injured. By making this dissection unnecessary, the procedure can be safer and may be accomplished by practitioners with average skills. Therefore, there is great benefit to a method that allows placement of a restrictive appliance that is semi-circumferential and avoids the posterior aspect of the abdomen.

SUMMARY OF THE INVENTION

Embodiments of the invention provide devices and methods for placing a band or other appliance around a hollow bodily organ such as the stomach without any skin incisions. In one alternative, a gastroscope is placed into the stomach and a hole is made through the stomach wall. This provides a route outside of the stomach. Another similar hole is made on the other side of the stomach, about opposite to the first hole. The band is passed out of one hole and the passed end is retrieved by a retractor that has been passed out of the other hole and has been advanced around the outside of the stomach. When the band has been docked or otherwise connected to the retractor, the band is drawn back into the hole which the retractor was passed through. The process is then repeated by passing the retractor in the other direction around the stomach and retracting the other end of the band into the transgastric hole. The ends of the band are then attached by one of a variety of means, and the band that now runs around the outside of the stomach, is tightened around the stomach. The gastric holes are closed by suturing or other fixation device. The band may be included within the closure, which restricts the subsequent movement or slippage of the band over time.

In one embodiment of the present invention, a method is provided for placing and/or affixing a semi-circumferential appliance on the wall surface of a hollow bodily organ by moving through the wall to the other side of the wall. The hollow bodily organ may be one from the stomach, the intestine, the airway, the esophagus. Exemplary embodiments of placing through the wall surface comprise piercing, cutting, injecting and/or burning through the wall to create on opening passage to the other surface of the wall. The moving through the wall may occur at the location of the placing an appliance on the wall surface or it may occur at a location away from the placing an appliance on the wall surface Further, the appliance may be affixed to hollow organ wall by any one or more of suturing, stapling, gluing, tissue-welding, encapsulating, marcupializing, engulfing with tissue, tacking, tethering.

In another aspect of the present invention, an apparatus for placing a semi-circumferential appliance on a wall surface of a hollow bodily organ is provided. In an exemplary embodiment, such an apparatus may include an elongate shaft member having proximal and distal ends, a transmission disposed at a distal end of the shaft member, a user manipulable handle disposed at the proximal end of the shaft member and cooperatively linked to the transmission for operation thereof, and a semi-circular member having two opposed ends to define an opening therebetween, The semi circular member is mounted on and cooperates with the transmission for opening and closing of the opposed ends.

In a further alternative embodiment, the transmission opens and closes the opposed ends of the semi-circular member in response to rotation of the handle. Additionally, the transmission can be configured to release the semi-circular member in response to further rotation of the handle. The opposed ends of the semi-circular member may also include elements for piercing tissue.

DETAILED DESCRIPTION OF THE INVENTION

Figure 1:
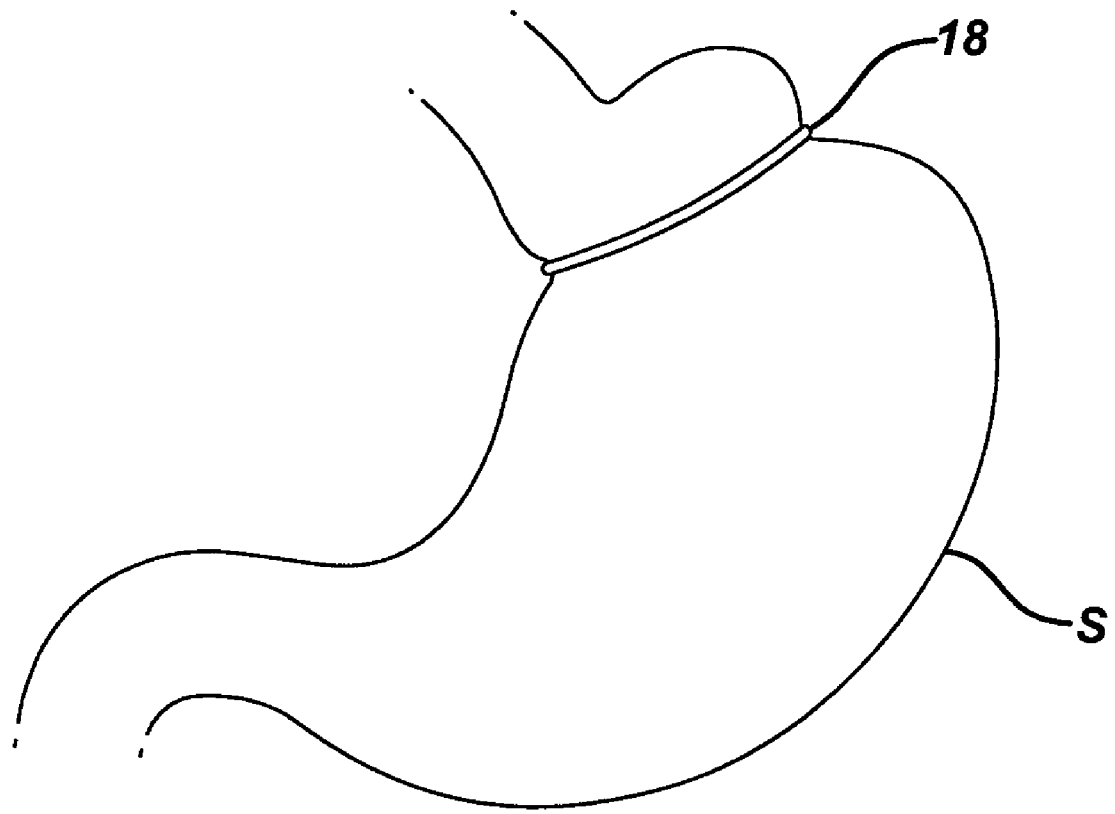
FIG. 1 illustrates an example of a hollow body organ, in this case a stomach, with a device according to an embodiment of the present invention deployed thereon.

Embodiments of the present invention include an implant device configured to be implanted onto a lumen of a hollow bodily organ or conduit including the stomach, the intestine, the heart, the airway, the vein, the artery, the esophagus, the aorta, and/or the renal artery without creating an incision outside the body, wherein the implant can be configured and/or adjusted to constrict or reduce the stomach or other hollow bodily organ or conduit. An exemplary embodiment is shown in FIG. 1, wherein a band 18 is deployed around a patients stomach S. Embodiments of the invention further include a method for less invasively deploying such devices through natural body orifices.

Exemplary method steps includes the steps of placing an instrument such as an endoscope into the stomach or other organ or conduit through the mouth or other natural orifice, making a hole through the stomach or hollow organ or conduit wall, directing a flexible wire or tube at least partially around the outside of the stomach and re-entering the stomach at or near the point of the original exit from the stomach. Suitable endoscopic devices including tissue manipulating functionality are disclosed, for example, in U.S. Pat. Nos. 6,494,888 and 6,663,639, which are incorporated by reference in there entirety herein. The hole can be made by cutting, piercing, burning with RF energy directed into the tissue through a conductive tip on the wire or needle knife, or similar method know by those practitioners of the art.

Figure 2A:
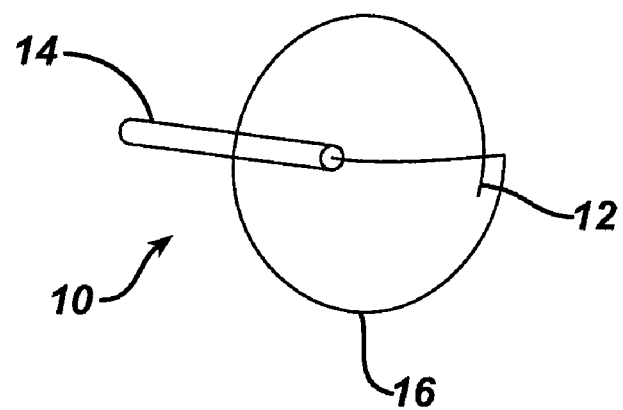
FIGS. 2A and B illustrate an embodiment of a guide wire according to the present invention.
Figure 2B:
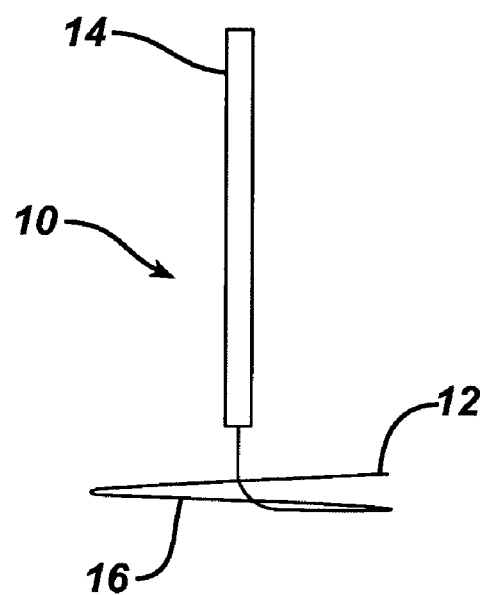
Figure 4:
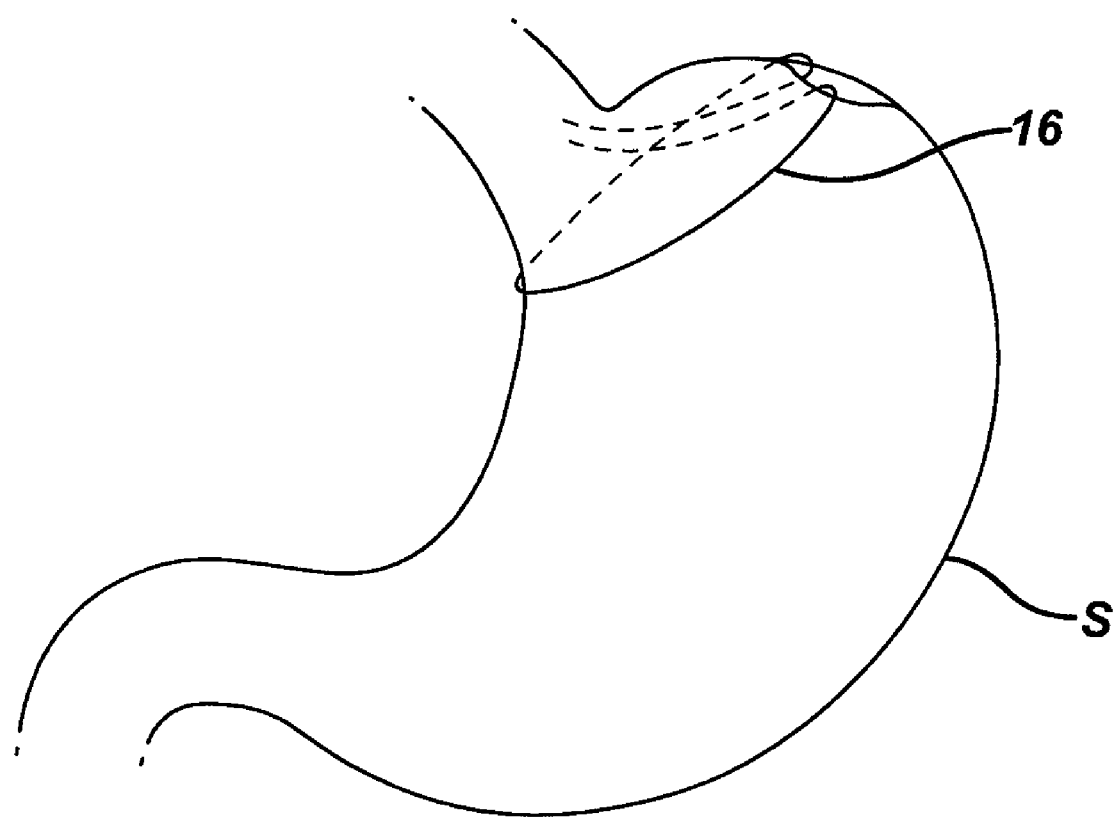
FIG. 4 illustrates placement of a guide wire according to an embodiment of the invention in a patient's stomach.

Referring to FIGS. 2A and B, an exemplary embodiment of a guide wire device 10 is shown. Guide wire device 10 has a tip 12 that may be energized with RF energy, sharpened or otherwise configured to puncture through the wall of a hollow bodily organ from the inside. By manipulating handle 14, the wire 16 of the guide wire device 10 is moved through and outside the wall of the organ around the organ as shown in FIG. 4. Throughout such a procedure, the user manipulable, proximal end of the handle 14 remains outside of the mouth or other natural body orifice, for example through an endoscopic device as mentioned above.

Figure 3A:
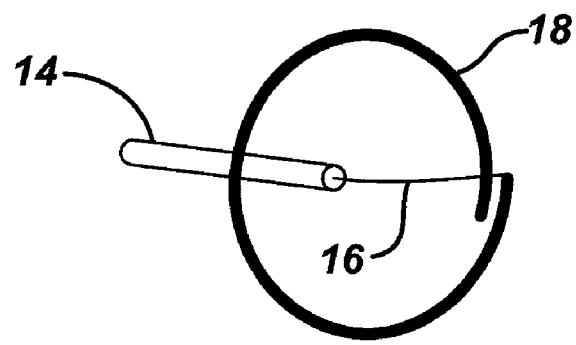
FIGS. 3A and B illustrate a band placed over a guide wire according to one embodiment of the present invention.
Figure 3B:
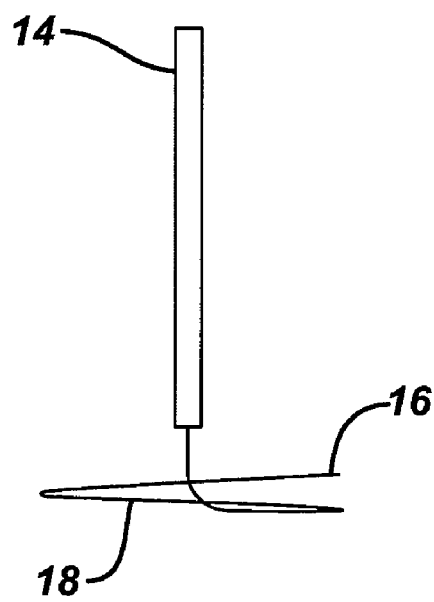

Once the guide wire 16 is placed around the hollow body organ, a restricting band 18 may be advanced there over as shown in FIGS. 3A and B. Alternatively, a guide tube first may be extended over the guide wire and the restricting band deployed either inside or outside the guide tube.

Figure 6:
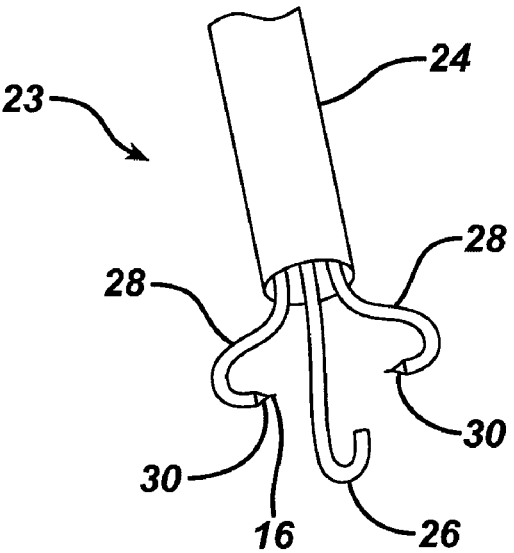
FIG. 6 illustrates a distal end of a device according to an embodiment of the present invention for deploying a guide wire and restricting band.

An exemplary device 23 for placement of guide wire 16 and appliance 18 is illustrated in FIG. 6. As shown, outer tube 24 is used to deliver endoscope 26 and manipulable arms 28 through the esophagus and cardiac orifice into the stomach. Manipulable arms 28 may include tissue piercing elements 30 at each distal end and may be hollow to permit delivery of the guide wire 16. As one possible alternative, such a device may be configured largely as described in the previously incorporated '888 or '639 patents.

Using device 23, appropriate locations on the organ wall can be visualized with endoscope 26 and pierced by the tissue piercing elements on manipulable arms 28. Guide wire 16 can then be advance through the organ wall and around the outer surface of the organ. Means for directing the guide wire are discussed below. Upon return to the exit opening or a secondary opening created by piercing elements 30, guide wire 16 may be recaptured by manipulable arms 28, or an alternative device, such as a grasper arm inserted through tube 24 can be used for this purpose. With the end of the guide wire 16 recaptured, it can be returned external to the hollow organ (and patient) and the appliance 18 guided into place therewith.

Figure 7A:
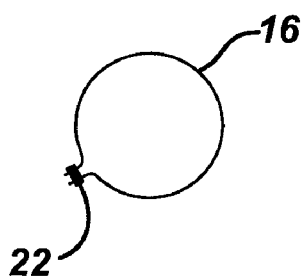
FIGS. 7A and 7B illustrate alternative embodiments of guide elements and securing elements according to the present invention.
Figure 7B:
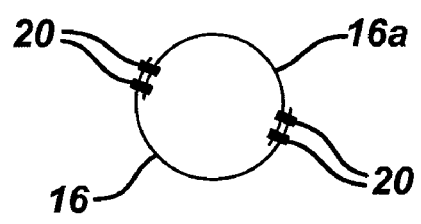

In another embodiment of the present invention, the wire 16 or guide tube can be made to exit the stomach and reenter the stomach at points partially around the outside of the stomach. Manipulable arms 28 and piercing elements 30 provide an exemplary embodiment for accomplishing such a procedural alternative. Another wire or guide tube 16a is then used to reenter the previous exit hole or entry hole where it is then directed at least partially around the stomach. Two close ends of the two wires or tubes or one wire and one tube are then joined. Such joining may be accomplished, for example by magnets 20 attached to each wire end or by twisting or clipping the ends together, or by placing the wire inside of the nearby tube end and crimping them together with one or more fasteners 22 as shown in FIGS. 7A and B. The wire or tube may be pulled so that the junction of the wires and/or tubes is pulled out of the stomach and a single wire or tube goes all the way around the stomach. This wire or tube is then used to place an appliance around the stomach over or through the tube such that the wire or tube is used as a rail-like or tunnel-like guide for placement of the appliance.

The guide wire or tube may encounter resistance or encounter tissue through which it must pass. In that case, the wire or tube may be rotated, vibrated axially at audible or sub-ultrasonic frequencies, to act similarly to a jack-hammer but at a much smaller scale, or may be alternately flexed in one direction and then another at some frequency in order to make passage possible.

Figure 5A:
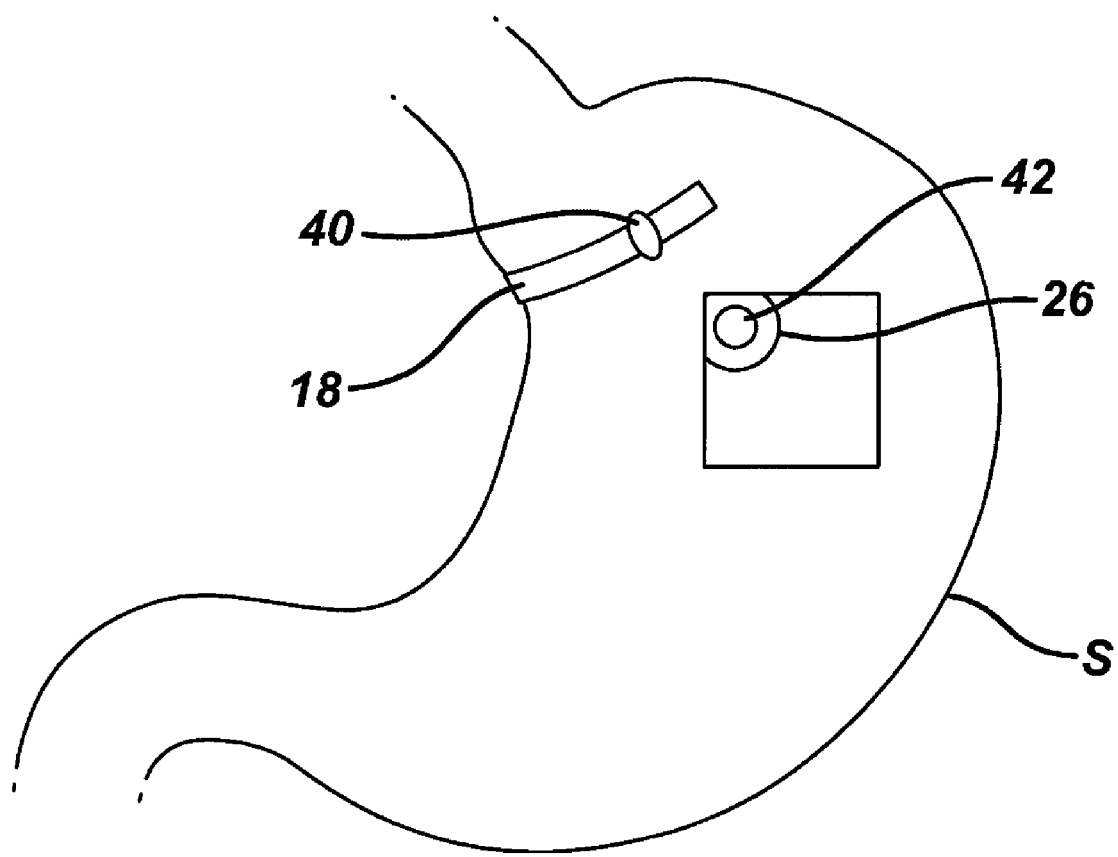
FIG. 5A is a side view of a patient's stomach, with a square shaped cut-away to reveal the interior, illustrating a further embodiment of the invention including a band and magnets positioned on the outside of a patient's stomach.
Figure 5B:
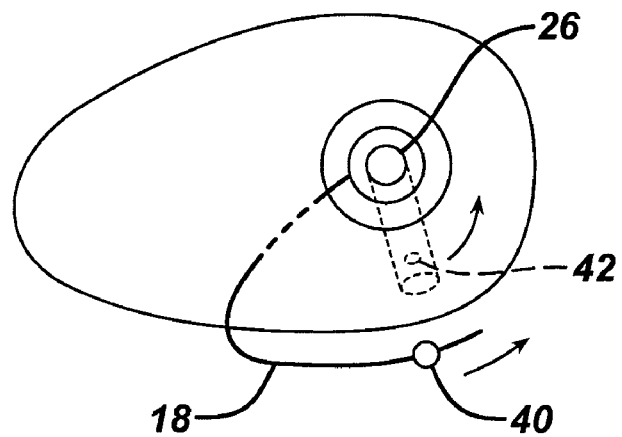
FIG. 5B illustrates a cross-section of a patient's stomach including an embodiment of the invention as shown in FIG. 5A.

Alternatively, as shown in FIGS. 5A and B, the guide element may be magnetically driven without additional openings through the organ wall. Here, guide element 16 or band 18 is provided with a magnetic element 40 at or near the advancing end. In this view, a square cut-away of the wall of the stomach S is shown to reveal the endoscope 26 within the interior of the stomach. Using complementary magnets 42 placed on the endoscope 26, or other manipulable device, the band may be driven around the organ by rotating the endoscope. The arrangement is also illustrated in the cross-sectional top view of FIG. 5B.

The guide wire or tube may also be configured with a tip that allows axial expansion for passage through tissue. This dissection may be accomplished through expanding a balloon on the guide wire or tube in order to create a space to loosen the tissue, deflating the balloon and advancing the guise wire or tube, re-expanding the balloon, and repeating as often as necessary to accomplish passage. Alternatively, the tip of the guide wire or tube may have a scissor-like member, where the method entails opening and closing while pushing the guide wire or tube, in order to accomplish passage.

In another embodiment, the guide wire or tube may have a light source to allow it to be seen through the stomach wall as it is passing around the stomach, the method involving directing and redirecting the guide wire or tube based on seeing the light contained on the guide wire or tube through the wall of the organ.

In one embodiment, the appliance has channels through which the wire or tube are threaded. The appliance is then directed around the hollow bodily organ or conduit until it is positioned around the stomach or bodily organ by pushing or pulling it around the stomach, either with the wire as the puller or pusher, or with a pusher or puller that is also placed over or through the guide wire or tube. The ends of the appliance may be connected directly or by threading one end through the other end to form a loop or by other similar method such as loop and hook fastener, snaps, magnets, tying the ends together, suturing the ends together or other method know to practitioners of the art. The length of the appliance in part determines the amount of constriction of the hollow organ around which it is placed. The amount of tightening determines the amount of constriction.

In another embodiment, the appliance is placed around the organ directly without the need for an additional guide wire or tube, which is integrated into the appliance.

In another embodiment, the appliance may be adjusted after placement by injecting a fluid into the appliance. This injection can be accomplished with a needle directed through the stomach wall directly into the appliance or into a reservoir attached to the appliance. Alternatively, it can also be adjusted by applying energy through capacitive coupling between a coil on the appliance and a coil inside the organ, said energy being used to move a piezo-actuator or motor that contracts the length of the band.

In another embodiment, the amount of constriction of the hollow bodily organ can be varied after placement of the band by allowing the band to swell or shrink through absorbing or losing fluid from its environment. A hydrogel or other polymeric or fibrous material will absorb fluid when the appliance is loose, and will lose fluid when the appliance is tight, as a sponge does when it is squeezed.

The appliance may be fixed in place on the organ by suturing, stapling, folding tissue over it and affixing the tissue by suturing, stapling, or using a Plicator® such as from NDO Surgical, INC. in what may be described as marcupialization, tacking, gluing or tethering.

Figure 8:
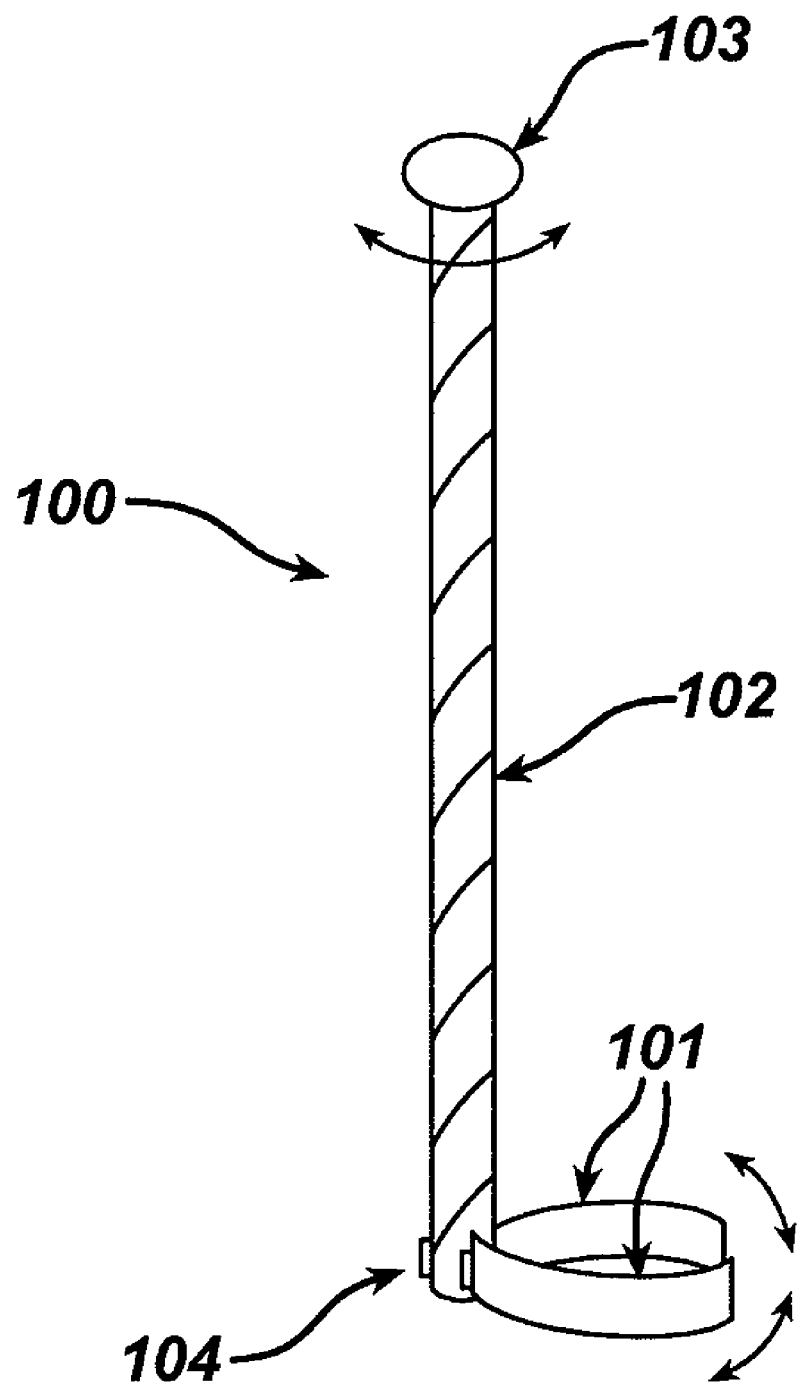
FIG. 8 illustrates a device for deploying a semi-circumferential band according to an alternative embodiment of the invention.
Figure 9:
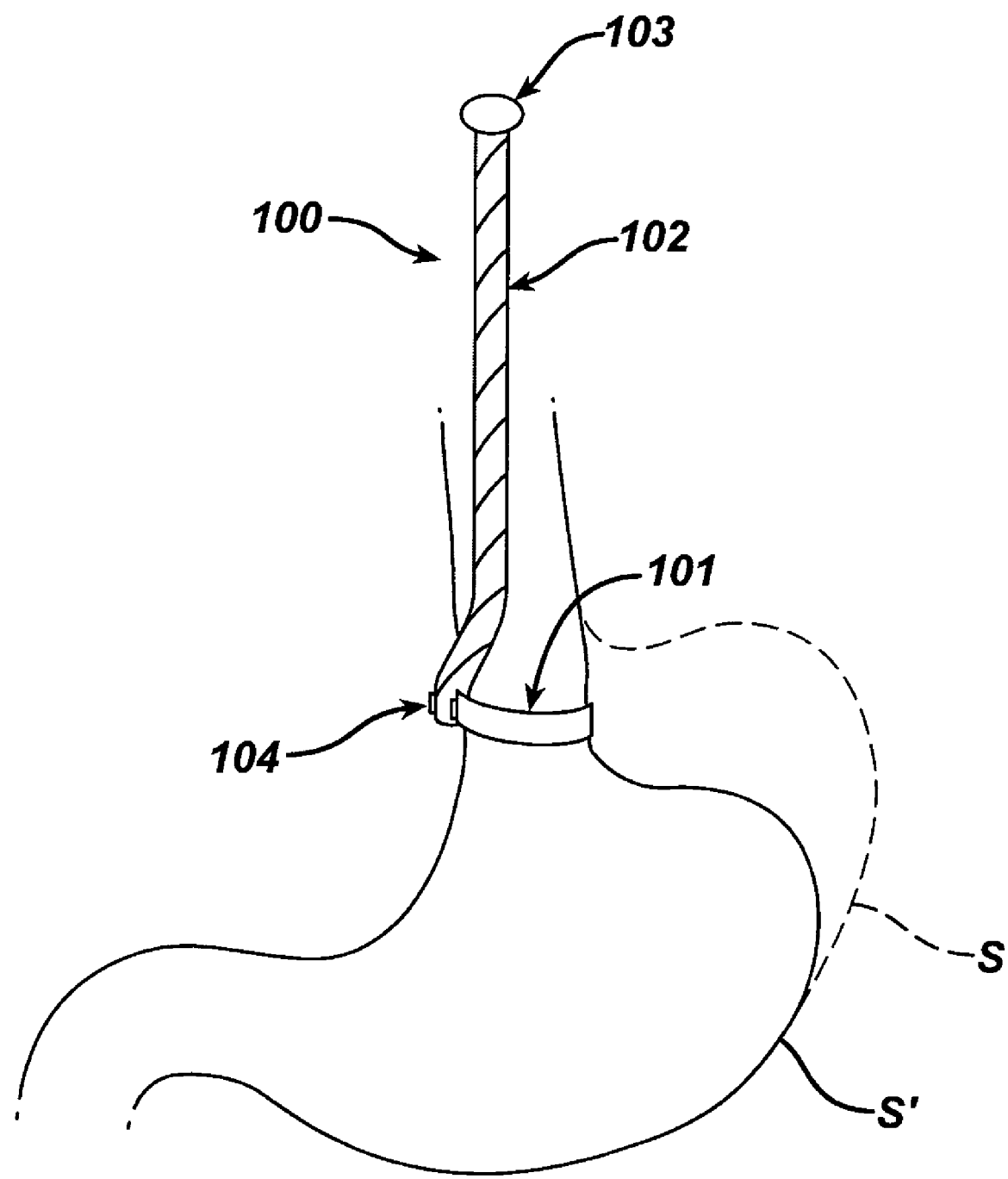
FIG. 9 illustrates the device of FIG. 8 in a deployed state on the stomach in one embodiment.
Figure 10:
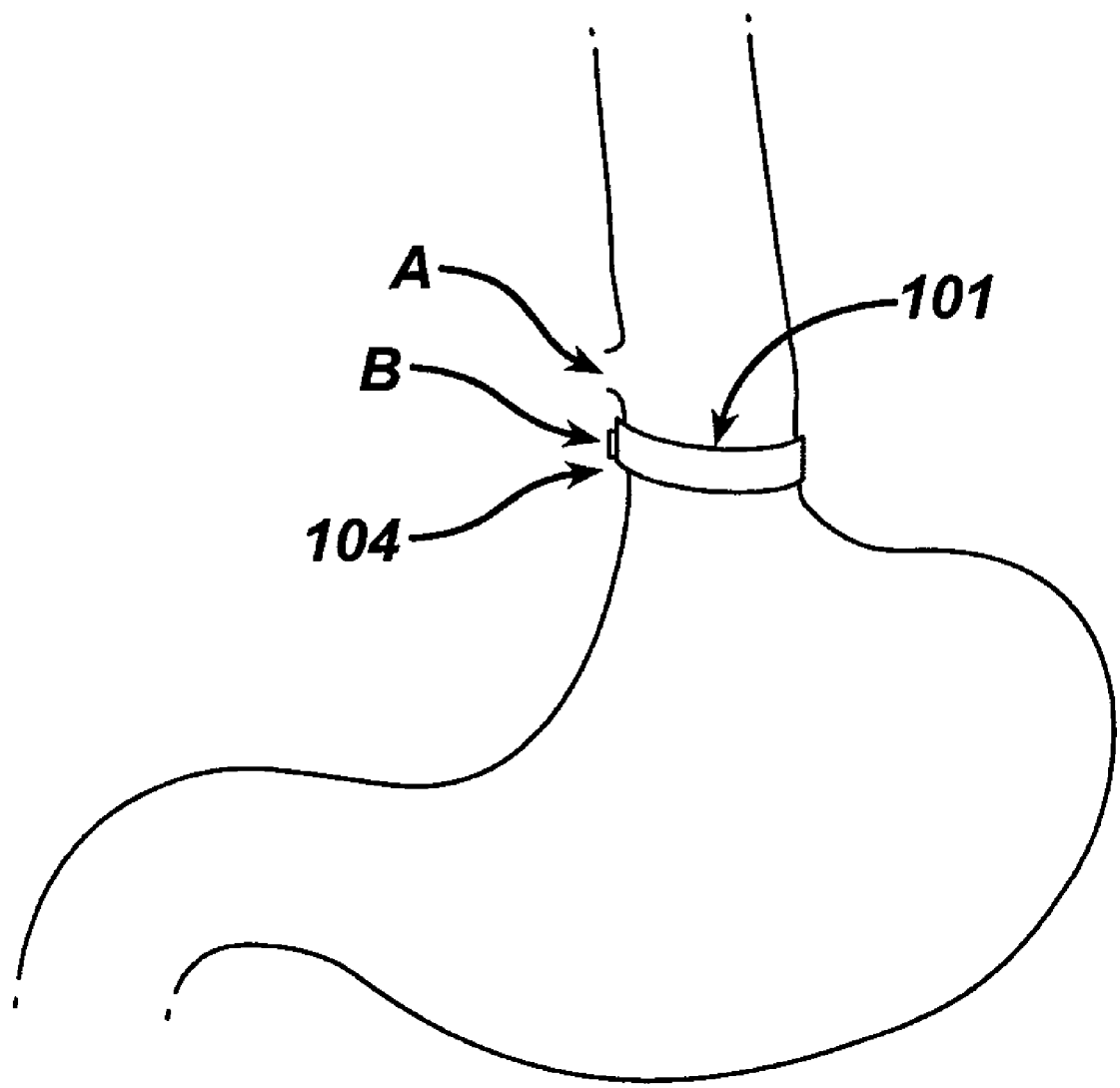
FIG. 10 illustrates a deployed semi-circumferential band as in FIGS. 8 and 9, and two deployment positions, in accordance with further alternative embodiments of the invention.

In a further alternative embodiment, a deployment device 100 including a semi-circumferential band as illustrated in FIGS. 8-10 may be employed. Device 100 includes a semi-band 101 that may be formed of a semi-rigid bio compatible material so as to facilitate maintaining shape after deployment. Device 100 also includes a proximal extending shaft 102 with a handle 103 configured to be positioned outside of a delivery tube 24 or other endoscopic device for manipulation and deployment. At the distal end of shaft 102, transmission 104 is linked to cooperate with band 101 to close and release it from the shaft. In an exemplary embodiment, rotation of handle 103 actuates transmission 104 to close and release band 101. Turning the handle 103 in an opposite direction prior to the release point operates to open band 101 through transmission 104 for repositioning.

In use, device 100 is inserted transorally in cooperation with a suitable delivery device such as tube 24 or other endoscopic device. An opening through the gastric wall may be made below the cardiac orifice and opposite the fundus as depicted in FIG. 9. With band 101 thus positioned on stomach S, it can be closed via rotation of handle 103 outside the esophagus, as described above. Once closed, the wall of the stomach is pulled in and constricted by band 101 to position S' as shown.

FIG. 10 illustrates two possible deployment positions for band 101, wherein location A shows the placement position through the stomach wall distant from the band 101 placement site, and location B represents the method of placing the band 101 through a hole in the wall that will be directly under the band 101 when it is closed. FIG. 10 also shows the band 101 with the handle 103 detached there from and in the open position. The band 101 may be closed by reattachment of handle 103 or may incorporate internal adjustment means such as disclosed for the full circumferential band described in applicant's co-pending U.S. patent application Ser. No. 12/107,717 also filed Apr. 22, 2008, the contents of which are incorporated herein by reference thereto.

What is claimed:

1. A method of placing a semi-circumferential appliance on a wall surface of a hollow bodily organ, comprising
    placing a manipulable device through a natural body opening into a hollow bodily organ, said manipulable device including at a distal end a deployable semi-circumferential appliance extending in a plane that is angularly oriented relative to a longitudinal axis of said manipulable device;
    moving said semi-circumferential appliance through a wall surface of the hollow bodily organ to another surface of the wall;
    closing the semi-circumferential appliance around at least a portion of the hollow bodily organ to capture a portion thereof;
    detaching the semi-circumferential appliance from the manipulable device; and
    removing the manipulable device from the hollow bodily organ.

2. The method as in claim 1, wherein the hollow bodily organ is one of the stomach, intestine, airway, and esophagus.

3. The method as in claim 1, wherein moving through the wall comprises piercing, cutting, injecting and/or burning through the wall to create on opening passage to the other surface of the wall.

4. The method as in claim 1, wherein moving through the wall occurs at a location of the placing the appliance on the wall surface.

5. The method as in claim 1, wherein moving through the wall occurs at a location away from the placing the appliance on the wall surface.

6. The method as in claim 1, further comprising affixing the semi-circumferential appliance to the organ wall.

7. The method as in claim 6, wherein affixing includes at least one of the following actions: suturing, stapling, gluing, tissue-welding, encapsulating, marcupializing, engulfing with tissue, tacking, and tethering.

* * * * *